(12) United States Patent
Lambert et al.

(10) Patent No.: US 11,375,949 B2
(45) Date of Patent: Jul. 5, 2022

(54) HYDRATION STATE INDICATOR

(71) Applicant: KONINKLIJKE PHILIPS N.V., Eindhoven (NL)

(72) Inventors: Nicolaas Lambert, Waalre (NL); Denny Mathew, Eindhoven (NL); Marcel Cornelis Dirkes, The Hague (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 351 days.

(21) Appl. No.: 15/536,918

(22) PCT Filed: Dec. 8, 2015

(86) PCT No.: PCT/EP2015/078908
§ 371 (c)(1),
(2) Date: Jun. 16, 2017

(87) PCT Pub. No.: WO2016/096520
PCT Pub. Date: Jun. 23, 2016

(65) Prior Publication Data
US 2017/0340274 A1    Nov. 30, 2017

(30) Foreign Application Priority Data

Dec. 18, 2014   (EP) ..................................... 14198810

(51) Int. Cl.
*A61B 5/00* (2006.01)
*A61B 5/0537* (2021.01)

(52) U.S. Cl.
CPC .......... *A61B 5/4875* (2013.01); *A61B 5/0537* (2013.01); *A61B 5/443* (2013.01);
(Continued)

(58) Field of Classification Search
CPC ..... A61B 5/4875; A61B 5/6833; A61B 5/443; A61B 5/0537
See application file for complete search history.

(56) References Cited

U.S. PATENT DOCUMENTS 3,802,842 A *  4/1974  Lange .................... C12Q 1/54
                                                    436/169
4,717,378 A    1/1988  Perrault
(Continued)

FOREIGN PATENT DOCUMENTS

CN    101382484 A    3/2009
JP    05468654 B2    4/2014

OTHER PUBLICATIONS

Fenzl, C., Hirsch, T., & Wolfbeis, O. S. (2014). Photonic crystals for chemical sensing and biosensing. Angewandte Chemie International Edition, 53(13), 3318-3335. (Year: 2014).*
(Continued)

*Primary Examiner* — Puya Agahi

(57) ABSTRACT

There is provided a hydration state indicator. The hydration state indicator comprises a watertight shell; a semi-permeable membrane configured to permit the passage of water molecules and to block the passage of molecules of at least one solute; a water-absorbent indicator layer enclosed by the shell and the membrane; and output means configured to provide an output. The water-absorbent indicator layer has a predetermined osmotic strength. The volume of at least one part of the indicator layer is variable in dependence on the water content of the indicator layer. The output is variable in dependence on the volume of the at least one part of the indicator layer.

12 Claims, 2 Drawing Sheets

(52) U.S. Cl.
CPC ............ *A61B 5/6833* (2013.01); *A61B 5/742* (2013.01); *A61B 5/7405* (2013.01); *A61B 5/7455* (2013.01); *A61B 5/7415* (2013.01)

(56) References Cited

U.S. PATENT DOCUMENTS

| | | | |
|---|---|---|---|
| 4,732,153 | A | 3/1988 | Phillips |
| 4,756,314 | A | 7/1988 | Eckenhoff |
| 5,465,713 | A | 11/1995 | Schoendorfer |
| 5,667,798 | A | 9/1997 | Royds |
| 5,890,489 | A * | 4/1999 | Elden ............... A61B 5/14532 128/898 |
| 5,898,004 | A * | 4/1999 | Asher ................. G02B 26/002 436/518 |
| 6,559,351 | B1 * | 5/2003 | Eakin ............... A61F 13/00055 602/56 |
| 6,961,175 | B2 | 11/2005 | Toda |
| 7,105,225 | B2 * | 9/2006 | Birkholz ............ G09F 3/0291 428/354 |
| 7,154,019 | B2 * | 12/2006 | Mishima ................ A61F 13/42 604/361 |
| 7,498,802 | B2 * | 3/2009 | Takahata ............ G01D 5/2066 324/207.15 |
| 7,643,874 | B2 * | 1/2010 | Nitzan ................. A61N 1/0448 604/20 |
| 7,743,642 | B2 * | 6/2010 | Chiba .................... B32B 27/32 73/29.04 |
| 8,196,809 | B2 * | 6/2012 | Thorstensson .......... A61F 13/42 235/375 |
| 8,721,562 | B2 | 5/2014 | Abreu |
| 9,341,588 | B2 * | 5/2016 | Palazzotto ............. B82Y 15/00 |
| 10,136,831 | B2 * | 11/2018 | Heikenfeld .......... A61B 5/4266 |
| 2004/0070824 | A1 * | 4/2004 | Toda ...................... G02B 5/003 359/452 |
| 2007/0233028 | A1 | 10/2007 | Roe |
| 2008/0215024 | A1 | 9/2008 | Diehl |
| 2009/0009193 | A1 * | 1/2009 | Hsiung ................ G01N 27/223 324/664 |
| 2009/0036763 | A1 | 2/2009 | Brauker |
| 2009/0157024 | A1 * | 6/2009 | Song ...................... G01N 21/80 604/361 |
| 2010/0112680 | A1 * | 5/2010 | Brockwell ................ A61B 5/07 435/287.9 |
| 2010/0174187 | A1 * | 7/2010 | Cohen-Solal ........ A61B 5/4869 600/438 |
| 2012/0003685 | A1 | 7/2012 | Kritzman |
| 2013/0245388 | A1 | 9/2013 | Rafferty et al. |
| 2014/0200538 | A1 | 7/2014 | Euliano |
| 2015/0335288 | A1 * | 11/2015 | Toth ..................... A61B 5/6833 600/373 |
| 2016/0159842 | A1 * | 6/2016 | Evans ................ A61B 5/14552 600/364 |

OTHER PUBLICATIONS

Wang, Z., Zhang, J., Li, J., Xie, J., Li, Y., Liang, S., . . . & Zhang, H. (2011). Colorful detection of organic solvents based on responsive organic/inorganic hybrid one-dimensional photonic crystals. Journal of Materials Chemistry, 21(4), 1264-1270. (Year: 2011).*

Lin, J., Tang, Q., Wu, J., & Hao, S. (2007). The synthesis and electrical conductivity of a polyacrylate/graphite hydrogel. Reactive and Functional Polymers, 67(4), 275-281. (Year: 2007).*

Mulder, D. J., Schenning, A. P. H. J., & Bastiaansen, C. W. M. (2014). Chiral-nematic liquid crystals as one dimensional photonic materials in optical sensors. Journal of Materials Chemistry C, 2(33), 6695-6705. (Year: 2014).*

Dhont, J. (2005). An introduction to dynamics of colloids. Amsterdam: Elsevier, pp. 107-170. (Year: 2005).*

Van der Linden, H. J., Herber, S., Olthuis, W., & Bergveld, P. (2003). Stimulus-sensitive hydrogels and their applications in chemical (micro) analysis. Analyst, 128(4), 325-331. (Year: 2003).*

Sun, J. Y., Keplinger, C., Whitesides, G. M., & Suo, Z. (2014). Ionic skin. Advanced Materials, 26(45), 7608-7614. (Year: 2014).*

Jhon, M. S., & Andrade, J. D. (1973). Water and hydrogels. Journal of biomedical materials research, 7(6), 509-522. (Year: 1973).*

Sheppard Jr, N. F., Lesho, M. J., McNally, P., & Francomacaro, A. S. (1995). Microfabricated conductimetric pH sensor. Sensors and Actuators B: Chemical, 28(2), 95-102. (Year: 1995).*

Chen, C., Zhu, Y., Bao, H., Zhao, P., Jiang, H., Peng, L., . . . & Li, C. (2011). Solvent-assisted poly (vinyl alcohol) gelated crystalline colloidal array photonic crystals. Soft Matter, 7(3), 915-921. (Year: 2011).*

Furumi, S. (2013). Self-assembled organic and polymer photonic crystals for laser applications. Polymer journal, 45(6), 579. (Year: 2013).*

Mocanu, A., Rusen, E., & Diacon, A. (2013). Optical properties of the self-assembling polymeric colloidal systems. International Journal of Polymer Science, 2013. (Year: 2013).*

Guiseppi-Elie, A. (2010). Electroconductive hydrogels: synthesis, characterization and biomedical applications. Biomaterials, 31(10), 2701-2716. (Year: 2010).*

Pissis, P., & Kyritsis, A. (1997). Electrical conductivity studies in hydrogels. Solid State Ionics, 97(1-4), 105-113. (Year: 1997).*

Aguirre, C. I., Reguera, E., & Stein, A. (2010). Tunable colors in opals and inverse opal photonic crystals. Advanced Functional Materials, 20(16), 2565-2578. (Year: 2010).*

Wang, J., Zhang, Y., Wang, S., Song, Y., & Jiang, L. (2011). Bioinspired colloidal photonic crystals with controllable wettability. Accounts of Chemical Research, 44(6), 405-415. (Year: 2011).*

Lavrentovich, O. D. (2011). Liquid crystals, photonic crystals, metamaterials, and transformation optics. Proceedings of the National Academy of Sciences, 108(13), 5143-5144. (Year: 2011).*

Fernandez L.A. et al., "Design and Characterization of an Osmotic Sensor for the Detection of Events Associated with Dehydration and Overhydration", Wearable Sensors and Health Monitoring Systems, IEEE Journal of translational Engineering in Health and Medicine, vol. 1, 2013, pp. 2279105-2700317.

* cited by examiner

HYDRATION STATE INDICATOR

CROSS-REFERENCE TO RELATED APPLICATIONS

This patent application claims the priority benefit under 35 U.S.C. § 371 of international patent application no. PCT/EP2015/078908, filed Dec. 8, 2015, which claims the benefit of European Patent Application No. EP14198810.5, filed on Dec. 18, 2014, the entire disclosure of which is incorporated by reference as if set forth in its entirety herein.

TECHNICAL FIELD OF THE INVENTION

The invention relates to a hydration state indicator for visually indicating the hydration state of a substance, and in particular relates to a hydration state indicator for visually indicating the hydration state of a body part of a subject.

BACKGROUND TO THE INVENTION

A person will experience dehydration when their water loss exceeds their water intake. This is usually caused by exercise or disease. For example, some elderly people have a chronically reduced thirst reflex. Dehydration more severe than a three to four percent decrease in body water can result in fatigue, dizziness, severe headaches, physical and mental deterioration, and even organ failure in chronic cases. A decrease in body water of more than fifteen to twenty-five percent is invariably fatal. Fluid overload is also dangerous. It commonly happens in hospital as a result of intravenous therapy, and can lead to dangerous edema and permanent kidney injury.

The hydration state of the body is currently not easily assessed. Both dehydration and fluid overload correspond to a deviation from normal osmotic balance in the body. Various types of laboratory equipment for measuring osmotic state exist; however such systems are generally bulky and require fluid samples (i.e. blood samples). It is therefore difficult to monitor the osmotic state of a subject's body over a period of time and/or outside of a clinic using conventional techniques.

L. A. L. Fernandes et. al., "Design and Characterization of an Osmotic Sensor for the Detection of Events Associated With Dehydration and Overhydration"; IEEE JTEHM 1: 2700309 describes an osmotic sensor intended for body measurement applications. The sensor comprises a small, rigid structure (a reference chamber) filled with a reference fluid of a constant osmotic strength. Water molecules can flow into or out of the reference chamber through a semi-permeable membrane. The osmotic pressure within the structure therefore depends on the relative osmotic strengths of the reference fluid and an external fluid with which the semi-permeable membrane is in contact. When the device is implanted into the body of a subject, or attached to their skin, the osmotic pressure in the reference chamber therefore varies with the level of hydration of the subject. The osmotic pressure in the reference chamber is measured by a pressure transducer having an electronic read out.

This device suffers from several disadvantages. If implanted it is invasive and therefore not suitable for widespread use. However; the rigid nature of the device (required by the pressure-sensing technique employed) means that it is difficult to achieve a good seal against a subject's skin during external use. Additionally, the membrane ceases to function properly after a certain period of exposure to the reference solution, limiting the operational lifetime of the device to less than two-weeks. Furthermore, the complex structure of the device and its use of electronic components make it relatively costly to manufacture.

A simple to use, non-invasive and cost-effective means of detecting the hydration state of a subject would therefore be desirable. Preferably such a device would be suitable for prolonged monitoring of hydration state, and could be used by any person who is at risk of either dehydration or fluid overload.

SUMMARY OF THE INVENTION

According to a first aspect of the invention, there is provided a hydration state indicator. The hydration state indicator comprises a watertight shell; a semi-permeable membrane configured to permit the passage of water molecules and to block the passage of molecules of at least one solute; a water-absorbent indicator layer enclosed by the shell and the membrane; and output means configured to provide an output. The water-absorbent indicator layer has a predetermined osmotic strength. The volume of at least one part of the indicator layer is variable in dependence on the water content of the indicator layer. The output is variable in dependence on the volume of the at least one part of the indicator layer.

In some embodiments, an optical property of the indicator layer is variable in dependence on the volume of the at least one part of the indicator layer. In some such embodiments the output means comprises a transparent window provided in the shell.

In some embodiments the indicator layer comprises a layer of water-absorbent material having a first refractive index; a first interface between the layer of water-absorbent material and a first adjacent material; and a second interface between the layer of water-absorbent material and a second adjacent material. In some such embodiments the thickness of the layer of water absorbent material is variable in dependence on its water content. In some such embodiments the first adjacent material and the second adjacent material each have a refractive index which is different to the first refractive index, such that the indicator layer functions as a dichroic filter. In some such embodiments the first adjacent material and/or the second adjacent material comprises a further layer of water-absorbent material, wherein the thickness of the further layer of water absorbent material is variable in dependence on its water content. In some embodiments the first adjacent material is comprised in the shell. In some embodiments the second adjacent material is comprised in the semi-permeable membrane.

In some embodiments the indicator layer comprises a photonic colloidal crystal in which particles of a first material are suspended in a second material. In some such embodiments the second material is water-absorbent. In some such embodiments the separation between the particles of the first material is variable in dependence on the water content of the second material.

In some embodiments the indicator layer comprises a cholesteric liquid crystal material comprising a plurality of cholesteric liquid crystals which each have a director axis. In some such embodiments a period of variation of the director axes of the cholesteric liquid crystals in the material is variable in dependence on the water content of the cholesteric liquid crystal material.

In some embodiments the hydration state indicator comprises a light-diffusing material. In some such embodiments the light-diffusing material is comprised in the shell. In some embodiments the light-diffusing material is comprised in a light-diffusing layer provided between the indicator layer and the shell. In some embodiments the light-diffusing material is comprised in a light-diffusing layer provided on an external surface of the shell.

In some embodiments an electrical property of the indicator layer is variable in dependence on the volume of the at least one part of the indicator layer. In some such embodiments the output means comprises a display electrically connected to the indicator layer. In some such embodiments the output means alternatively or additionally comprises a vibrator electrically connected to the indicator layer. In some such embodiments the output means alternatively or additionally comprises a speaker electrically connected to the indicator layer. In some such embodiments the output means alternatively or additionally comprises a wireless communications transmitter electrically connected to the indicator layer.

In some embodiments in which an electrical property of the indicator layer is variable in dependence on the volume of the at least one part of the indicator layer, the electrical property is conductance. In some such embodiments the indicator layer comprises particles of a first material suspended in a second material. In some embodiments the second material is water-absorbent and the separation between the particles of the first material is variable in dependence on the water content of the second material. In some embodiments one of the first and second materials has relatively low or no conductance and the other of the first and second materials has relatively high conductance. In some embodiments the indicator layer comprises salt ions in a water-absorbent matrix material.

In other embodiments in which an electrical property of the indicator layer is variable in dependence on the volume of the at least one part of the indicator layer, the electrical property is capacitance. In some such embodiments the indicator layer comprises first and second conductive plates. In some embodiments the indicator layer comprises a layer of non-conductive material between the first and second conductive plates. In some embodiments the non-conductive material is water-absorbent and the thickness of the non-conductive material is variable in dependence on its water content.

In some embodiments the output means is arranged to display an image and/or text in response to a volume change of the at least one part of the indicator layer. In some embodiments in which an optical property of the indicator layer is variable in dependence on the volume of the at least one part of the indicator layer, the indicator layer comprises a first region and an adjacent second region. In some such embodiments the optical property of the first region changes by a first amount in response to a given volume change of the at least one part of the indicator layer, and the optical property of the second region changes by a second, different amount in response to the given volume change.

In some embodiments one or more of the shell, the semi-permeable membrane, and the indicator layer are flexible.

In some embodiments the hydration state indicator further comprises an attachment means. In some such embodiments the attachment means comprises an adhesive layer provided on a surface of the semi-permeable membrane and/or the shell. In some such embodiments the attachment means alternatively or additionally comprises a strap attached to the shell. In some such embodiments the attachment means alternatively or additionally comprises an item of clothing attached to the shell.

In some embodiments the predetermined osmotic strength is substantially equal to the osmotic strength of healthy human tissue.

There is also provided, according to a second aspect of the invention, an indicator layer arranged for use in a hydration state indicator according to the first aspect, wherein the indicator layer comprises a water-absorbent material having a predetermined osmotic strength, and wherein the volume of at least one part of the indicator layer is variable in dependence on the water content of the indicator layer. In some embodiments the indicator layer is arranged to be enclosed between the watertight shell and the semi-permeable membrane. In some embodiments the indicator layer is arranged to cooperate with the output means to provide the output.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION

Figure 1:
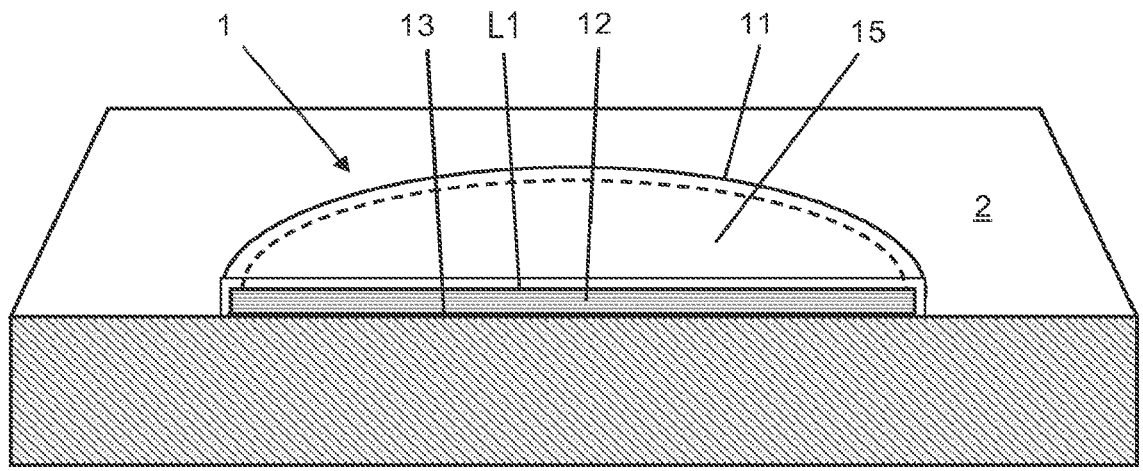
FIG. 1 is a perspective cross-sectional view of a hydration state indicator in use on a subject, according to a first embodiment of the invention.
Figure 2:
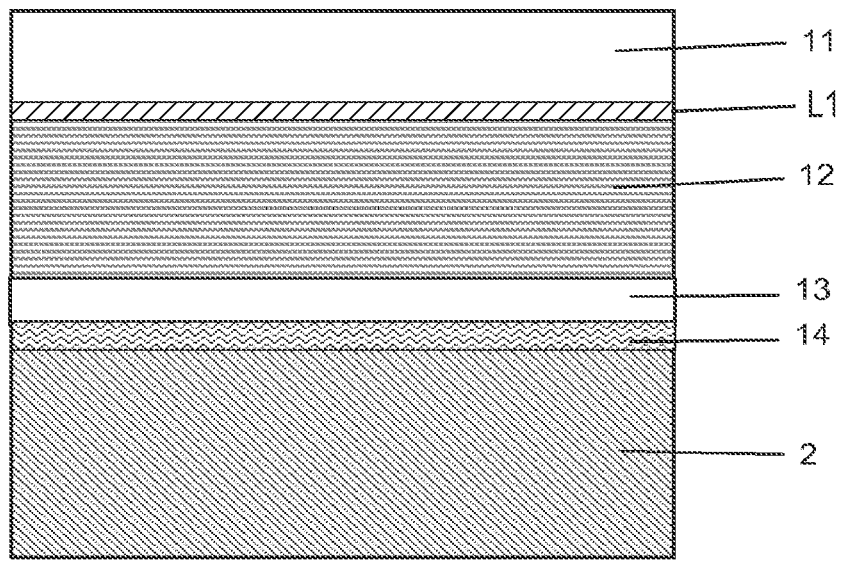
FIG. 2 is an enlarged cross-sectional view of the hydration state indicator of FIG. 1.

FIG. 1 shows a hydration state indicator 1 according to a first exemplary embodiment of the invention, applied to the skin 2 of a subject. FIG. 2 is an enlarged cross-section through the hydration state indicator 1, which more clearly shows the layered structure of the indicator 1. In this example the hydration state indicator 1 is an adhesive skin patch which visually indicates the osmotic state of the skin 2 to which it is applied (which correlates with the osmotic state of the underlying tissue, and thus with the hydration state of the subject).

The hydration state indicator 1 comprises a substantially watertight shell 11, which covers the outer surfaces of an indicator layer 12. The inner surface (i.e. the surface which is adjacent to the subject's skin) of the indicator layer is covered by a semi-permeable membrane 13. The indicator layer 12 is completely enclosed by the shell 11 and the semi-permeable membrane 13. The hydration state indicator 1 also includes an output means 15, which in the specific example of FIG. 1 comprises a transparent window in the shell 11 (alternatively, the entire shell 11 could be transparent). In use the hydration state indicator 1 is attached to the skin 2 by an adhesive layer 14 (not visible in FIG. 1). The area covered by the hydration state indicator is approximately 2 $cm^2$, although other sizes would be equally suitable. Preferably the area covered by the hydration state indicator is between 5 $mm^2$ and 1000 $mm^2$. It will be appreciated that a larger area can advantageously make it easier for a subject to view the hydration state indicator 1, and can also make the hydration state indicator 1 more accurate (because a larger area of tissue is sampled). However, if the hydration state indicator is too large it will be difficult to achieve good conformance to the subject's skin, and it will be difficult to avoid significant bending of the hydration state indicator, which can negatively affect its output (depending on the particular nature of the indicator layer used).

The shell 11 comprises a layer which creates a substantially hermetic seal against the skin 2. (It should be noted that it is not necessary for the shell 11 to be perfectly watertight or for the seal to be perfectly hermetic. Instead, it is sufficient that the shell blocks water transport significantly more than the skin and the other components of the hydration state indicator 1). The substantially hermetic seal ensures that the indicator layer 12 does not dry out and that osmotic balance between the indictor layer 12 and the subject's tissue is maintained. The shell 11 includes a transparent window 15. The window 15 allows incident light to pass through it to the indicator layer 12, and it also causes the indicator layer 12 to be visible to the subject when the hydration state indicator 1 is in use. When used in combination with an indicator layer which changes appearance in dependence on its water content, the window 15 therefore functions as an output means for the hydration state indicator 1. In some embodiments the size and/or material of the shell is selected to permit the indicator layer 12 to increase in thickness. In preferred embodiments the indicator layer 12 is permitted to increase in thickness by at least 20%. In preferred embodiments the indicator layer is very thin, meaning that very little flexibility of the shell material is required in order to accommodate the anticipated increases in thickness of the indicator layer (which will typically be not more than 30%). In preferred embodiments the shell 11 is flexible. In some embodiments the shell comprises an elastic material. This advantageously accommodates swelling of the indicator layer 12 and improves conformance of the patch to the subject's body surface, particularly during movement. In some embodiments the shell 11 comprises a transparent plastic foil. Any transparent and watertight bio-compatible film could, in principle, be used, including bio-compatible or food grade polypropylene (PP), polyethylene terephthalate (PET), polyethylene (PE), polyvinyl acetate (PVA), polyvinyl butyral (PVB), etc.

The structure of the semi-permeable membrane 13 is such that it allows the passage of water molecules but blocks molecules of a particular solute. In the example of FIG. 1, the semi-permeable membrane is a NAFION® (a sulfonated tetrafluoroethylene based fluoropolymer-copolymer) membrane which blocks the passage of salt ions. It will be appreciated, however, that various other membranes known in the art could be used instead, including for example membranes made of nanoporous expanded polytetrafluoroethylene (ePTFE), nanoporous cellulose ester, or nanoporous alumina. Different membranes block different solutes, so it is expected that the membrane material will be chosen in dependence on the particular intended application of the hydration state indicator 1. For example, a membrane which permits the passage of water molecules and salt ions but blocks the passage of proteins could be employed in a hydration state indicator which is configured to monitor the protein concentration (i.e. the oncotic pressure) of a subject's blood. In some embodiments the semi-permeable membrane 13 includes micro-needles that penetrate the skin surface (as are known in the art for use with drug-releasing skin patches). Advantageously, providing such micro-needles can improve water exchange between the subject's tissue and the indicator layer 12, and can therefore shorten the response time of the hydration state indicator 1. In some embodiments the size and/or material of the semi-permeable membrane 13 is selected to permit the indicator layer 12 to increase in thickness by at least 20%. In preferred embodiments the semi-permeable membrane 13 is flexible. In some embodiments the semi-permeable membrane 13 comprises an elastic material. This advantageously accommodates swelling of the indicator layer 12 and/or improves conformance of the patch to the subject's body surface, particularly during movement.

The adhesive layer 14 can comprise any suitable adhesive known in the art. In the embodiment of FIG. 1, the adhesive layer 14 comprises a layer of a hydrogel adhesive. The adhesive should be able to cope with a very humid local environment, so that it can maintain adhesion even if the subject's skin becomes wet. In preferred embodiments the adhesive layer is flexible. In some alternative embodiments, the adhesive layer is not present and alternative means is provided to attach the hydration state indicator to the subject's skin. In some such embodiments a strap (e.g. a wristband, or chestband) is provided, fixed to the shell. In other embodiments the hydration state indicator is incorporated into an item of clothing, such as a tightly-fitting vest.

The indicator layer 12 is water-absorbent and is structured such that its volume is dependent on its water content. Furthermore, the composition of the indicator layer is tailored (e.g. by the incorporation of a certain amount of a particular solute—in this example, salt—into the material of the indicator layer) such that osmotic strength of the indicator layer 12 is substantially equal to the osmotic strength of healthy human tissue (i.e. tissue which is not dehydrated or experiencing fluid overload). In preferred embodiments the indicator layer 12 is flexible, to facilitate conformance of the hydration state indicator 1 to the subject's body surface. Flexible indicator layers can change thickness when bent, which (depending on the particular mechanism used by the indicator layer 12 to indicate water-content) can affect the output of the indicator layer. In preferred embodiments the indicator layer is thin compared to the expected bending radius, to minimise this effect. Using a thinner indicator layer can also advantageously reduce the response time of the hydration state indicator 12.

In the example of FIG. 1, the indicator layer is configured to behave like a dichroic filter. In some embodiments this is achieved by an indicator layer comprising a single layer of material which has a different refractive index to the material of the shell 11 and to the material of the semi-permeable membrane 13. In such embodiments, incident light is partially reflected (and thus partially transmitted) by the interface between the indicator layer 12 and the shell 11, and the transmitted part of the incident light is then partially reflected (and thus partially transmitted) by the interface between the indicator layer 12 and the semi-permeable membrane 13. The two reflected parts interfere with each other and the extent of this interference depends on (among other factors) the distance between the two interfaces, and therefore on the thickness of the indicator layer 12. The colour of the reflected light depends on the extent of the interference, and thus the colour of the indicator layer (as viewed by the subject) will change in dependence on the thickness of the indicator layer. Since the volume of the material of the indicator layer (and therefore its thickness) changes in dependence on its water content, the colour change observed by the subject correlates with the water content of the indicator layer. Suitable materials for the indicator layer of this embodiment include water-absorbent gels, rubbers and plastics materials. Suitable examples of such materials include, for example, acrylic hydrogel, hydrophilic polyether block amide and polyvinyl alcohol. In order to achieve the dichroic behaviour described above, each layer comprised in the indicator layer 12 must have a thickness of the order of a wavelength of light or less. To achieve such thin films, technologies like spin coating, spray coating or vapour deposition coating can be employed, with the shell 11 or membrane 13 as the substrate.

The default colour of the indicator layer 12 (i.e. its colour when it is in osmotic balance with underlying tissue, thus indicating a healthy hydration state) can be set by selecting the thickness of the indicator layer. In some embodiments the color change is not homogeneous across the entire visible area of the indicator layer 12. Instead, in some embodiments the indicator layer 12 is configured such that one or more regions do not change colour, or change colour to a different degree to adjacent regions. In some such embodiments the regions of different colour change behavior are configured such that a visible message or icon emerges at particular hydration states. For example, a pictogram of a cup could appear when the hydration state indicator 1 detects that the subject's tissue is dehydrated (i.e. when the water content of the indicator layer 12 is lower than the default level). Regions of differing colour change behavior can be implemented, for example, by preventing water from being absorbed by one or more regions of the indicator layer 12, by performing an additional polymerisation step on one or more regions of the indicator layer material (e.g. by local exposure to high temperature or a chemical agent), or by simply printing a reference color on to one or more regions of the indicator layer 12, membrane 13 or shell 11.

In some alternative embodiments the dichroic effect is achieved by providing a multi-layered indicator layer 12. In such embodiments the indicator layer 12 consists of two or more sub-layers, where each sub-layer has a different refractive index to the immediately adjacent sub-layer. In such embodiments there does not need to be (although there can be) a difference in refractive index between the indicator layer 12 and the shell 11, or between the indicator layer 12 and the semi-permeable membrane 13. In such embodiments it is not necessary for all of the sub-layers of the indicator layer 12 to be water-absorbent. Instead, alternating sub-layers of a water-absorbent material and a non-water-absorbent material can be used. It is, however, necessary for any sub-layers which are arranged between a water-absorbent sub-layer and the semi-permeable membrane 13 to permit the passage of water molecules therethrough. Suitable materials for a non-water-absorbent sub-layer include polyamide, NAFION® (a sulfonated tetrafluoroethylene based fluoropolymer-copolymer), ion-exchange materials, proton-exchange materials, and silicones. Many other plastics are water permeable to some extent, especially when very thin, and therefore could potentially be used (as mentioned above, all sub-layers of the indicator layer 12 must be very thin in order to achieve the dichroic effect). Non-water-absorbent sub-layers can be applied, for example, using spin coating, spray coating or vapour deposition coating. Alternatively, one or more of the non-water absorbent sub-layers could comprise a self-assembling membrane, such as a lipid bilayer.

Conventional dichroic filters are typically desired to be highly stable, and are therefore built from materials which have extremely low water uptake. Conventional methods used for the manufacture of dichroic filters are therefore unsuitable for producing the water-absorbent indicator layer 12. Instead, one or more sub-layers having well-defined thickness can be formed from flexible, water-absorbent materials such as those described above, using known multi-layer coating and lamination techniques. The flexibility of the preferred indicator layer materials means that the layer thickness can be fine-tuned by stretching.

In some alternative embodiments the indicator layer 12 comprises a photonic colloidal crystal. The photonic colloidal crystal is made up of insoluble particles of a first substance suspended in a second substance. The first substance could be, e.g., a monodisperse silica or a polymer. The optical properties of the photonic colloidal crystal depend, among other factors, on how closely packed the particles of the first substance are. The second substance is a water-absorbent material which changes volume in dependence on its water content. This means that the closeness of the particles, and thus the optical properties of the crystal, change in dependence on the water content of the second substance. Consequently the colour of the indicator layer (as viewed by the subject) will change in dependence on the water content of the second substance. In preferred embodiments the second substance is flexible. Suitable materials for the second substance include water-absorbent gels, rubbers and plastics materials such as, for example, acrylic hydrogel, hydrophilic polyether block amide, or polyvinyl alcohol. The default colour of a photonic colloidal crystal indicator layer can be set during manufacture by setting how closely-packed the particles of the first substance are.

In some alternative embodiments the indicator layer 12 comprises a cholesteric liquid crystal material. Suitable materials include, for example, hydroxypropyl cellulose or cholesteryl benzoate. A cholesteric liquid crystal (also known as a chiral nematic liquid crystal) is a liquid crystal with a helical structure, which is therefore chiral. Cholesteric liquid crystals organize in layers. There is no positional ordering within layers, but each layer has a director axis, which varies periodically between the layers. The period of this variation (i.e. the distance over which a full rotation of 360° is completed) determines the wavelength of light which is reflected by the cholesteric crystal material. The period of this variation can depend on the water content inside the crystal material. In some embodiments the cholesteric liquid is stabilized as droplets dispersed inside a polymer matrix. In such embodiments the polymer matrix has to be transparent and water-permeable. Suitable materials for the polymer matrix include, for example, polyamide, NAFION® (a sulfonated tetrafluoroethylene based fluoropolymer-copolymer), ion-exchange materials, proton-exchange materials, and silicones.

In some embodiments (not specifically illustrated) the hydration state indicator 1 additionally comprises means for the slow release of a perfusion enhancer (such as a nicotinate, or capsaicin). In some such embodiments the hydration state indicator 1 includes an additional layer containing the perfusion enhancer. In alternative embodiments the perfusion enhancer is comprised in the adhesive layer. In some embodiments the hydration state indicator 1 is heated, e.g. chemically or electrically. Suitable techniques for heating and/or incorporating a perfusion enhancer into the hydration state indicator 1 are known in the art, e.g. for use with heating plasters (such as the Elastoplast® ABC heat plaster). Advantageously, increasing the level of perfusion of the skin to which the hydration state indicator 1 is attached, by use of heat or a perfusion enhancer, can enhance the correlation between the output of the hydration state indicator 1 and the osmotic (or oncotic) state of the subject's blood.

In some embodiments (not specifically illustrated) the hydration state indicator 1 additionally comprises means for reducing the angle-dependence of the colour seen by the subject when looking at the hydration state indicator 1. In some such embodiments a light-diffusing layer L1 is included between the indicator layer 12 and the window 15 part of the shell 11 to mix the angles of the reflected light. In some embodiments the light-diffusing layer L1 comprises a diffuse plastic layer. Alternatively the window 15 part of the shell 11, and/or the indicator layer 12 can have light-diffusing properties. In some such embodiments the outer surface of the shell 11 is rough, to create a light diffusing effect. In some embodiments a layer L1 having a high-refractive index is included between the indicator layer 12 and the shell 11, to reduce the angle variation. Alternatively or additionally the window 15 part of the shell 11, and/or the indicator layer 12 can have a high-refractive index. Advantageously, if the colour of the indicator layer 12 does not vary significantly with viewing angle it is easier for the subject (or a healthcare professional) to accurately determine whether a colour change has occurred.

Figure 3:
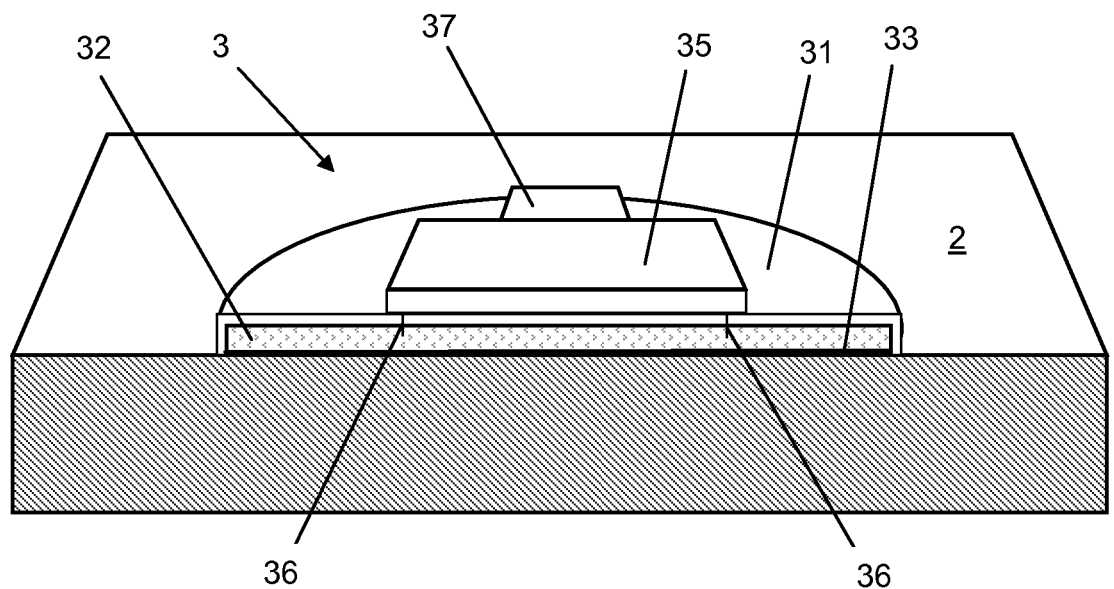
FIG. 3 is a perspective cross-sectional view of hydration state indicator in use on a subject, according to a second embodiment of the invention.

FIG. 3 shows a hydration state indicator 3 according to a second specific embodiment of the invention. The semi-permeable membrane 33 and adhesive layer 34 are the same as in the first specific embodiment. However; unlike in the first embodiment, in the second embodiment the indicator layer 32 is configured such that its electrical properties vary in dependence on its volume. The optical properties of the indicator layer 32 do not necessarily vary in dependence on its volume, and as such the shell 31 does not include a transparent window. Instead, in this embodiment the output means comprises a display 35 on the top surface of the hydration state indicator 3, which is electrically connected (e.g. by wires 36 which pass through the shell 31) to the indicator layer 32. The hydration state indicator 3 also includes a power source 37 electrically connected to the display 35. In some embodiments the power source 37 is a button cell battery. The display 35 is configured to change appearance in response to a change in an electrical property (which in the specific example of FIG. 3 is conductance, although it will be appreciated that other electrical properties could be used) of the indicator layer 32. In some embodiments the display 35 is an LCD display. In some embodiments the display is an OLED display. In some embodiments the display comprises a light source, such as one or more LEDs. In some such embodiments the light source is configured to flash in response to a change in an electrical property of the indicator layer 32. In some such embodiments the light source is configured such that the rate of flashing depends on a current value of the electrical property of the indicator layer 32. In some embodiments the display 35 is configured to change colour in response to a change in an electrical property of the indicator layer 32. In some embodiments the display 35 is configured to show a predefined message comprising an image and/or text in dependence on a current value of an electrical property of the indicator layer 32.

The indicator layer 32 comprises particles of a conductive material (e.g. graphite, gold spheres, etc.) suspended in a water-absorbent matrix material which has low or no conductivity. In some embodiments the volume of the matrix material changes in dependence on its water content. Suitable materials for indicator layers of such embodiments include water-absorbent gels, rubbers and plastics materials, including, for example, acrylic hydrogel, hydrophilic polyether block amide, and polyvinyl alcohol. In such embodiments changes in the volume of the matrix material alter the distances between the conductive particles, which in turn alters the conductance of the indicator layer 32. In some alternative embodiments the indicator layer 32 comprises salt ions in a water-containing matrix. In such embodiments water uptake into the indicator layer reduces the salt concentration of the layer, which in turn reduces its conductance. Alternative embodiments are also envisaged in which the indicator layer 32 comprises particles of a low-conductance material (e.g. silica or polymer) in a water-absorbent, conductive matrix (e.g. a salty hydrogel). Advantageously, the sensitivity of hydration state indicators according to such embodiments is higher than the sensitivity of hydration state indicators according to embodiments which use a salt-solution only for the indicator layer.

The conductance of the indicator layer 32 is detected by a circuit (not shown) connected to the display, which is configured to cause the appearance of the display to change in response to a change in the conductance of the indicator layer. For example, given a matrix material which swells as its water content increases, the conductance of the indicator layer will decrease (from the default level, which corresponds to a healthy hydration state) if the subject experiences fluid overload, due to water being pulled into the indicator layer and the resulting increased separation between the conductive particles. In this situation, some embodiments of the circuit are configured to cause the display 35 to show an indication warning the subject of fluid overload in response to a decrease in conductance of the indicator layer. Conversely, in response to an increase in the conductance of the indicator layer 32 the circuit would cause the display 35 to show an indication warning the subject of dehydration.

In some alternative embodiments the output means is configured to provide a tactile and/or audible output alternatively or additionally to providing a visual output. A tactile output can be provided, for example, by a vibrator electrically connected, via a circuit, to the indicator layer 32. In such embodiments the circuit can be configured to cause the vibrator to vibrate according to a first pattern and/or intensity if the conductance of the indicator layer decreases, and to vibrate according to a second pattern and/or intensity if the conductance of the indicator layer increases. An audible output can be provided, for example, by a speaker electrically connected, via a circuit, to the indicator layer 32. In such embodiments the circuit can be configured to cause the speaker to emit a first sound if the conductance of the indicator layer decreases, and to emit a second, different, sound if the conductance of the indicator layer increases. Advantageously, the circuit(s) can be configured such that the intensity and/or repetition frequency of the audible and/or tactile output increases with the severity of the dehydration or fluid overload being experienced by the subject.

In some embodiments the output means is configured to emit a wireless communications signal in dependence on variations in the conductance of the indicator layer 32, alternatively or additionally to providing a visual, tactile and/or audible output, using any suitable apparatus and techniques known in the art. The wireless communications signal can be received by, e.g. a smartphone belonging to the subject or to a healthcare professional, or by an electronic medical monitoring device. The receiving device can then advantageously generate an alert in response to changes in the subject's hydration state.

Figure 4:
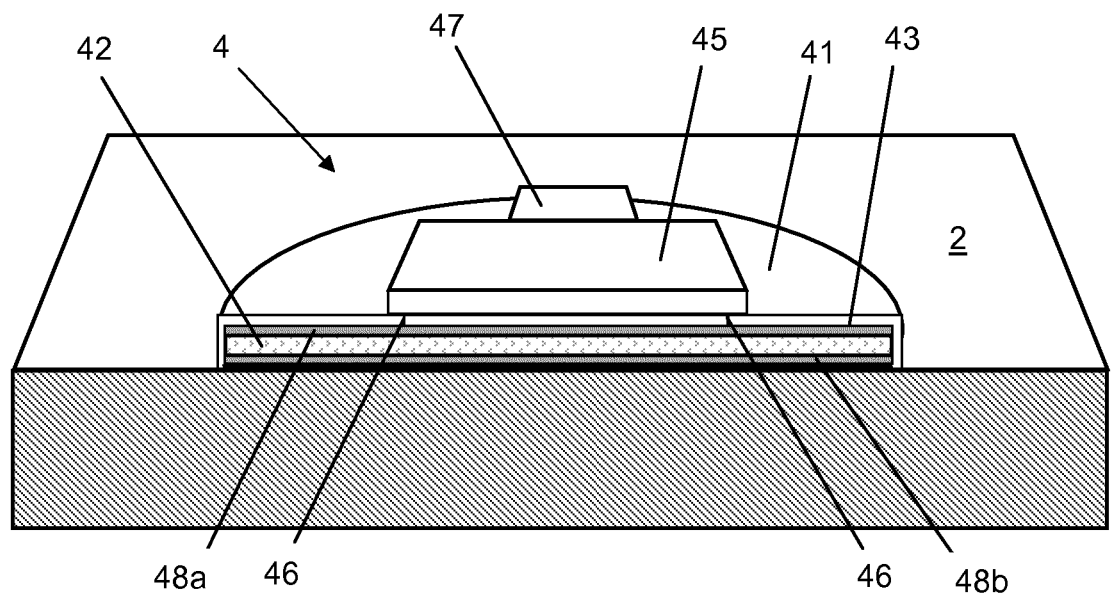
FIG. 4 is a perspective cross-sectional view of hydration state indicator in use on a subject, according to a third embodiment of the invention.

FIG. 4 shows a hydration state indicator 4 according to a third specific embodiment of the invention. The semi-permeable membrane 43 and adhesive layer 44 are the same as in the first specific embodiment. However; unlike in the first embodiment, the optical properties of the indicator layer 42 do not necessarily vary in dependence on its volume, and as such the shell 41 does not include a transparent window.

Instead, in this 30 embodiment the output means comprises a display 45 on the top surface of the hydration state indicator 4, which is electrically connected (e.g. by wires 46 which pass through the shell 41) to the indicator layer 42 (it will be appreciated that in other embodiments the output means can, alternatively or additionally, comprise any of the features described above in relation to the second embodiment). The display 45 is electrically connected to a power source 47, such as, for example, a button cell battery. In this embodiment the indicator layer 42 comprises a pair of conductive plates 48a, 48b, adjacent the top and bottom surfaces of a layer of non-conductive water-absorbent material having a predetermined osmotic strength, the volume of which is variable in dependence on its water content. The output means of the 5 hydration state indicator 4 comprises a display 45 (e.g. an LCD display or an OLED display) on the top surface of the hydration state indicator 4. The top conductive plate 48a is electrically connected (e.g. by wires 46 which pass through the shell 41) to the display 45. It will be appreciated that the conductive plates 48a, 48b, together with the water-absorbent material therebetween, form a variable capacitor. The capacitance of this variable capacitor 10 depends on the distance between the plates 48a, 48b, and therefore on the water content of the indicator layer 42. The display 45 is configured to change appearance (e.g. in any of the manners described above in relation to the second embodiment) in response to a change in the capacitance of this capacitor.

In embodiments of the hydration state indicator 4 where the indicator layer material swells as its water content increases, the capacitance of the capacitor formed by the plates 48a, 48b and the indicator layer 42 will decrease (from the default level, which corresponds to a healthy hydration state) if the subject experiences fluid overload, due to water being pulled into the indicator layer and the resulting increased separation between the conductive plates 48a, 48b. In this situation, some embodiments of the circuit are configured to cause the display 45 to show an indication warning the subject of fluid overload in response to a decrease in conductance of the indicator layer. Conversely, if the subject experiences dehydration, water will be pulled out of the indicator layer 42, the separation of the plates 48a, 48b will decrease, and consequently the capacitance will increase. In some embodiments the circuit is therefore configured to cause the display 45 to show an indication warning the subject of dehydration in response to an increase in the capacitance.

A procedure for using a hydration state indicator according to embodiments of the invention will now be explained. Although this procedure is explained with reference to the hydration state indicator 1 of the first embodiment, it will be appreciated that many aspects of the procedure are generally applicable, including to the hydration state indicators of the second and third embodiments. In use, the hydration state indicator 1 is attached, by means of the adhesive layer 14, to the skin of the subject. Preferably the attachment location is selected to have few sweat glands and to experience little or no change in surface shape when the subject moves. The output of the hydration state indicator 1 will be more representative of the subject's blood when the skin it is applied to is strongly perfused. For some applications it is therefore desirable to locate the hydration state indicator 1 on an area of skin which has many capillaries.

As described above, the osmotic strength of the indicator layer 12 is substantially equal to the osmotic strength of healthy human tissue. This means that if the skin and underlying tissue to which the hydration state indicator 1 is attached has a normal hydration state (i.e. not dehydrated and not experiencing fluid overload) then the skin 2 and indicator layer 12 will be in osmotic balance such that there is substantially no water transport between the two. The skin surface will typically be dry when the hydration state indicator 1 is attached, but because the shell 11 is substantially watertight, the skin surface will hydrate until it is in balance with the underlying tissue and the indicator layer. This is expected to take of the order of 1 hour). If the underlying tissue has a normal hydration state, the indicator layer 12 will not change in volume from its default state, and its colour will remain the default (healthy) colour.

If the subject becomes dehydrated, the osmotic strength of their tissue (and thus of the skin in contact with the hydration state indicator 1) will increase so that it is higher than the osmotic strength of the indicator layer 12. As a result, water will be pulled out of the indicator layer 12 and into the skin (through the semi-permeable membrane 13). The volume (and therefore the thickness) of the indicator layer 12 will change in accordance with its lower water content. The reduced thickness of the indicator layer 12 means that the distance between the interfaces which create the dichroic filtering effect is reduced, and consequently the colour of the indicator layer will change from the default colour. Conversely, if the subject experiences fluid overload, the osmotic strength of their tissue (and thus of the skin in contact with the hydration state indicator 1) will decrease so that it is lower than the osmotic strength of the indicator layer 12. As a result, water will be pulled from the skin 2 and into the indicator layer 12 (through the semi-permeable membrane 13). The volume (and therefore the thickness) of the indicator layer 12 will change in accordance with its higher water content. The increased thickness of the indicator layer 12 means that the distance between the interfaces which create the dichroic filtering effect is increased, and consequently the colour of the indicator layer will change from the default colour. Where a means for reducing the angle-dependence of the colour is not employed, the subject (or healthcare professional) should be instructed to always view the hydration state indicator 1 from the same angle (preferably at an angle roughly perpendicular to its upper surface).

The volume change experienced by the water-absorbent material in the indicator layer 12 is roughly proportional to the change in osmotic strength of the subject's tissue. The amount of volume change experienced for a given change in osmotic strength will depend on the particular water-absorbent material used. For a gel-like layer, for example, the percentage volume change can be roughly equal to the percentage change in osmotic strength of the subject's tissue. This in turn corresponds to a roughly equal percentage change in the wavelength of the light reflected from the indicator layer 12.

Variations in the osmotic strength of tissue of merely a few percent can be clinically relevant. For example, dehydration resulting in a change in osmotic strength of a few percent happens easily in sports. Dehydration resulting in a 10% change will cause health issue causes, and dehydration resulting in a 20% change will induce serious illness or death. It is not possible to visually detect such small changes using known colour-change humidity indicators and indicator dyes. However; a 10% wavelength increase changes yellow light into red light. The dichroic filtering effect employed by embodiments of the present invention therefore advantageously creates a significant colour change even when the osmotic strength of the subject's tissue has changed by only a few percent. As such, hydration state indicators according to embodiments of the present invention can reliably and distinctively distinguish between a healthy hydration state, minor dehydration (or fluid overload), and potentially dangerous dehydration (or fluid overload).

Water transport between the tissue and the indicator layer 12 occurs slowly because the process of diffusion through a semi-permeable membrane is inherently slow. The response time of a particular hydration state indicator 1 will depend on the thickness of the indicator layer 12 (or the thickness of the water-absorbent part of the indicator layer, if a multi-material indicator layer is used)—using a thinner indicator layer shortens the response time. In embodiments where the indicator layer thickness is of the order of 1 μm, it is expected that the time to reach osmotic balance will be of the order of 1 hour. As such, it is intended for the hydration state indicator 1 to be continuously worn by the subject for several hours, or even days.

Hydration state indicators according to particular embodiments of the invention are therefore particularly suitable for monitoring subjects who continuously have a high risk of dehydration, such as elderly patients who have a chronically reduced thirst reflex, and for monitoring subjects who continuously have a high risk of fluid overload, such as hospitalized patients who are receiving intravenous fluids. A hydration state indicator according to embodiments of the invention can be continuously worn by such subjects, in a location which is easily visible to the subject and/or to a healthcare provider, to make it clearly visible when the subject's hydration state begins to deviate from normal.

Hydration state indicators according to particular embodiments of the invention are also particularly suitable for monitoring the hydration state of subjects before, during and/or after exercise. Advantageously, such embodiments can prevent both dangerous dehydration, which can occur when sportspeople do not take on enough water during prolonged exercise, and fluid overload, which can occur when sportspeople take on too much water during or after exercise. It will be appreciated that sweat is typically produced by the skin during exercise; however this will not affect the function of the indicator layer. The composition of a subject's sweat (i.e. the ratio of water to salt) varies with their hydration level in a similar manner to the tissue, and less sweat is produced as a subject becomes dehydrated. Thus the osmotic strength of the skin 2 beneath the hydration state indicator 1 will increase in response to dehydration, even if the skin is producing sweat. It will be appreciated that embodiments of the hydration state indicator which are particularly intended for use during exercise should comprise an adhesive layer 14 which is able to maintain adhesion even if a substantial amount of sweat is produced, and should have a shape and/or size which permits them to be applied to a body part which experiences minimal sweating, and minimal bending when the subject moves.

There is therefore provided a hydration state indicator which can be worn continuously by a subject for an extended period of time and which is able to provide a clear visual indication of their hydration state.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A hydration state indicator comprising:
a watertight shell;
a semi-permeable membrane configured to permit the passage of water molecules and to block the passage of molecules of at least one solute;
a water-absorbent indicator layer enclosed by the shell and the membrane,
wherein the water-absorbent indicator layer has a predetermined osmotic strength, wherein the predetermined osmotic strength is substantially equal to the osmotic strength of healthy human tissue,
wherein the volume a first region of the water-absorbent indicator layer is variable in dependence on the water content of the water-absorbent indicator layer,
wherein the water-absorbent indicator layer provides a visual indication of hydration state which changes dynamically with the volume or water content of at least one part of the water-absorbent indicator layer,
wherein the volume of a second region of the water-absorbent indicator layer is variable in dependence on the water content of the water-absorbent indicator layer to a different degree than the first region
wherein the first region and the second region are disposed on the same layer of the water-absorbent indicator layer,
wherein an optical property of the water-absorbent indicator layer is variable in dependence on the volume of the at least one part of the water-absorbent indicator layer,
wherein the output means comprises a transparent window provided in the shell, and
wherein the water-absorbent indicator layer comprises a photonic colloidal crystal in which particles of a first material are suspended in a second material, wherein the second material is water-absorbent, and wherein the separation between the particles of the first material is variable in dependence on the water content of the second material; and
output means configured to provide an output which is variable in dependence on the volume of the at least one part of the water-absorbent indicator layer,
wherein at least one of the shell, a layer between the water-absorbent indicator layer and the shell, and an external surface of the shell comprise a light-diffusing material.

2. The hydration state indicator according to claim 1, wherein the water-absorbent indicator layer comprises:
a layer of water-absorbent material having a first refractive index, wherein the thickness of the layer of water absorbent material is variable in dependence on the water content of the layer of water absorbent material;
a first interface between the layer of water-absorbent material and a first adjacent material; and a second interface between the layer of water-absorbent material and a second adjacent material;
wherein the first adjacent material and the second adjacent material each have a refractive index which is different to the first refractive index, such that the water-absorbent indicator layer functions as a dichroic filter.

3. The hydration state indicator according to claim 2, wherein the first adjacent material and/or the second adjacent material comprises a further layer of water-absorbent material, wherein the thickness of the further layer of water absorbent material is variable in dependence on the water content of the layer of water absorbent material.

4. The hydration state indicator according to claim 1, wherein the water-absorbent indicator layer comprises a cholesteric liquid crystal material comprising a plurality of cholesteric liquid crystals which each have a director axis, wherein a period of variation of the director axes of the cholesteric liquid crystals in the material is variable in dependence on the water content of the cholesteric liquid crystal material.

5. A hydration state indicator comprising: a watertight shell;
a semi-permeable membrane configured to permit the passage of water molecules and to block the passage of molecules of at least one solute;
a water-absorbent indicator layer enclosed by the shell and the membrane,
wherein the water-absorbent indicator layer has a predetermined osmotic strength,
wherein the predetermined osmotic strength is substantially equal to the osmotic strength of healthy human tissue,
wherein the volume of at least one part of the water-absorbent indicator layer is variable in dependence on the water content of the water-absorbent indicator layer,
wherein an electrical property of the water-absorbent indicator layer is variable in dependence on the volume of the at least one part of the water-absorbent indicator layer,
wherein the water-absorbent indicator layer provides an indication of hydration state which changes dynamically with the volume or water content of at least one part of the water-absorbent indicator layer,
wherein an optical property of the water-absorbent indicator layer is variable in dependence on the volume of the at least one part of the water-absorbent indicator layer,
wherein the output means comprises a transparent window provided in the shell, and
wherein the water-absorbent indicator layer comprises a photonic colloidal crystal in which particles of a first material are suspended in a second material, wherein the second material is water-absorbent, and wherein the separation between the particles of the first material is variable in dependence on the water content of the second material; and
output means configured to provide an output which is variable in dependence on the volume of the at least one part of the water-absorbent indicator layer, wherein the output means comprises one or more of:
a display directly secured to an outer surface of the shell and electrically connected to the water-absorbent indicator layer;
a vibrator directly secured to the outer surface of the shell and electrically connected to the water-absorbent indicator layer; and
a speaker directly secured to the outer surface of the shell and electrically connected to the water-absorbent indicator layer.

6. The hydration state indicator according to claim 5, wherein the electrical property is conductance, and wherein the water-absorbent indicator layer comprises particles of a first material suspended in a second material, wherein the second material is water-absorbent and the separation between the particles of the first material is variable in dependence on the water content of the second material, and wherein one of the first and second materials has relatively low or no conductance and the other of the first and second materials has relatively high conductance.

7. The hydration state indicator according to claim 5, wherein the electrical property is conductance, and wherein the water-absorbent indicator layer comprises salt ions in a water-absorbent matrix material.

8. The hydration state indicator according to claim 5, wherein the electrical property is capacitance, and wherein the water-absorbent indicator layer comprises first and second conductive plates, and a layer of non-conductive material between the first and second conductive plates, wherein the non-conductive material is water-absorbent and the thickness of the non-conductive material is variable in dependence on the water content of the layer of water absorbent material.

9. The hydration state indicator according to claim 1, wherein the output means is arranged to display an image and/or text in response to a volume change of the at least one part of the water-absorbent indicator layer.

10. The hydration state indicator according to claim 9, wherein the water-absorbent indicator layer comprises a first region and an adjacent second region, wherein a first optical property of the first region changes by a first amount in response to a volume change of the at least one part of the water-absorbent indicator layer, and a second optical property of the second region changes by a second, different amount in response to the volume change of the at least one part of the water-absorbent indicator layer.

11. The water-absorbent indicator layer arranged for use in a hydration state indicator according to claim 1, wherein the water-absorbent indicator layer comprises a water-absorbent material having a predetermined osmotic strength, wherein the osmotic strength is substantially equal to the osmotic strength of healthy human tissue, and wherein the volume of at least one part of the water-absorbent indicator layer is variable in dependence on the water content of the water-absorbent indicator layer.

12. A hydration state indicator comprising: a watertight shell;
a semi-permeable membrane configured to permit the passage of water molecules and to block the passage of molecules of at least one solute;
a water-absorbent indicator layer enclosed by the shell and the membrane,
wherein the water-absorbent indicator layer has a predetermined osmotic strength,
wherein the predetermined osmotic strength is substantially equal to the osmotic strength of healthy human tissue,
wherein the volume a first region of the water-absorbent indicator layer is variable in dependence on the water content of the water-absorbent indicator layer,
wherein an optical property of the water-absorbent indicator layer is variable in dependence on the volume of the at least one part of the water-absorbent indicator layer, wherein the water-absorbent indicator layer provides a visual indication which changes dynamically with the volume or water content of at least one part of the water-absorbent indicator layer, wherein the water-absorbent indicator layer comprises a dichroic filter; and wherein the volume of a second region of the water-absorbent indicator layer is variable in dependence on the water content of the water-absorbent indicator layer to a different degree than the first region wherein the first region and the second region are disposed on the same layer of the water-absorbent indicator layer, wherein an optical property of the water-absorbent indicator layer is variable in dependence on the volume of the at least one part of the water-absorbent indicator layer, wherein the output means comprises a transparent window provided in the shell, and wherein the water-absorbent indicator layer comprises a photonic colloidal crystal in which particles of a first material are suspended in a second material, wherein the second material is water-absorbent, and wherein the separation between the particles of the first material is variable in dependence on the water content of the second material; and output means configured to provide an output which is variable in dependence on the volume of the at least one part of the water-absorbent indicator layer, wherein the output means comprises a transparent window provided in the shell, wherein at least one of the shell, a layer provided between the water-absorbent indicator layer and the shell, and an external surface of the shell, comprise a light-diffusing material.

\* \* \* \* \*